United States Patent [19]
Rosenstatter

[11] Patent Number: 6,159,004
[45] Date of Patent: Dec. 12, 2000

[54] INSTRUMENT HOLDER

[76] Inventor: Otto Rosenstatter, Matzing 105, A-5164 Seeham, Austria

[21] Appl. No.: 08/828,902

[22] Filed: Apr. 2, 1997

[30] Foreign Application Priority Data

Apr. 5, 1996 [DE] Germany .......................... 196 13 681

[51] Int. Cl.⁷ .................................. A61C 1/00; A61C 1/08
[52] U.S. Cl. .............................................. 433/29; 433/126
[58] Field of Search ........................... 433/29, 114, 115, 433/125, 126

[56] References Cited

U.S. PATENT DOCUMENTS

| | | | |
|---|---|---|---|
| 4,403,956 | 9/1983 | Nakanishi | 433/29 |
| 5,057,015 | 10/1991 | Fleer | 433/29 X |
| 5,074,785 | 12/1991 | Malata, Jr. | 433/29 |
| 5,332,389 | 7/1994 | Rosenstatter | 433/29 |
| 5,368,479 | 11/1994 | Lingenhole | 433/29 |
| 5,476,379 | 12/1995 | Disel | 433/29 |

*Primary Examiner*—Nicholas D. Lucchesi

[57] ABSTRACT

A dental instrument holder having a compressed air-driven motor can be connected via rotational coupling parts at any arbitrary angular position to a coupling piece, and has spaced-apart connecting elements for fluids and electrical energy and/or light.

19 Claims, 7 Drawing Sheets

INSTRUMENT HOLDER

BACKGROUND TO THE INVENTION

The present invention relates to an instrument holder or handpiece, especially a dental instrument holder.

The present invention is concerned with a dental instrument holder which comprises a working head such as a drill head mounted on a handle. The handle has a light outlet preferably lying in the vicinity of the working head and at least one further energy consuming component. The holder includes a coupling piece with a first connecting element that is required for emitting light from the light outlet, and at least one second connecting element radially spaced therefrom and serving to supply or remove waste material from the additional energy consuming component and which can be connected to a counter-coupling piece, through which an energy supply cable is connected to the instrument holder.

In known dental instrument holders, coupling pieces are provided for connection to a supply cable, which in the same way as the corresponding counter-coupling piece on the supply cable have a central fluid connecting part for waste air and further eccentric or off-centred connecting elements, for example for compressed air, power, light, etc. With these known instrument holders the instrument holder can be connected to the counter-coupling piece of the supply cable only in a certain angular position, which requires particular attention.

SUMMARY OF THE INVENTION

The present invention provides a dental instrument of the type referred to above, in which the coupling piece is detachably connected via a rotational coupling to the handle, which coupling has a handle-side or coupling part formed on the handle and a connection-side or coupling part formed on the coupling piece, one of these rotational coupling parts being provided with a coupling pin and the other of these rotational coupling parts being provided with a complementary coupling bore, so that the coupling pin and coupling bore can be displaced relative to one another in the axial direction and rotated relative to one another in the circumferential direction, and wherein a central light guide channel is provided in the coupling pin, which channel is axially aligned with a light outlet window in the floor or bottom wall of the coupling bore, or vice versa, and wherein an eccentric connecting line is provided in the coupling pin or in a wall surrounding the coupling bore, the end of which connecting line adjacent to the other rotational coupling part is connected via a coupling means rotationally symmetrical relative to the rotational coupling axis to a working line of the handle leading from the coupling means to the further energy consumer, or is connected to a connection line running between the coupling means and the second connecting element.

The instrument holder of the present invention has the advantage that it can be connected in any arbitrary angular position to a supply cable.

With the instrument holder according to the invention a further rotational coupling is provided in addition to the known coupling that can be engageably inserted only in a predetermined angular position, one rotational coupling part being provided on the coupling piece, and the other rotational coupling part being provided on the handle of the instrument holder. This rotational coupling has a centric coupling means for light and an eccentric rotationally symmetrical coupling means for supplying or removing spent material from a further energy consumer (for example a compressed air operated drive), so that the handle can be mounted in an arbitrary angular position on the coupling piece. This installation procedure can thus be carried out blind without having to exercise any particular care or attention. Also, it is sometimes advantageous when working with the instrument holder if the latter can be rotated about the handle axis without the supply cable becoming twisted.

Advantageous developments of the invention are disclosed in the sub-claims.

Preferably, a device is provided for axially locking the coupling piece and handle when the rotational coupling parts are fully engaged. This allows additional rotational coupling between the handle and coupling part can also be axially loaded.

Preferably, the locking device has at least one radially movable locking lug that is carried by one of the rotational coupling parts, and also has an all-round locking groove that is formed on the other of the rotational coupling parts and that cooperates with the locking lugs. This allows the handle to be releasably locked on the coupling piece in a mechanically particularly simple manner.

Preferably, the locking device has two diametrically opposite locking lugs that similarly cooperate with the locking groove. This allows the handle to be locked symmetrically relative to the handle axis.

Preferably, the locking lugs are carried by actuating arms that lie flush on the outside of that one of the rotational coupling parts carrying the locking lugs. This has the advantage of simple operation of the locking device.

Preferably, the locking lugs are carried by a locking sleeve that at least partially overlaps a radially set-back surface section of that one of the rotational coupling parts carrying the locking lugs and is coupled with this rotational coupling part to execute joint axial movement. In this way, the catch or locking lugs as well as the carrying actuating arms are mounted in a simple manner on the coupling piece. Also, the locking device is designed so as to be particularly compact in the radial direction.

Preferably, the further energy consumer is a fluid consumer, wherein the coupling pin and coupling bore are sealed with respect to one another and together define a coupling space in which terminate the connecting line formed in the coupling pin and the connecting line leading to a second connecting element. This permits the supply or removal of waste from a fluid consumer.

Preferably, the rotational coupling part containing the coupling bore with a circumferential surface set back relative to the outer surface of the coupling piece cooperates tightly with a circumferential wall at least partially overlapping the latter, of the rotational coupling part carrying the coupling pin. This provides a particularly good external seal of the rotational coupling.

Preferably, the rotational coupling part provided with the coupling bore has an end section of reduced diameter compared to the set-back surface, so as to define a coupling space between the aforementioned circumferential wall of the rotational coupling part carrying the coupling pin and this end section, which coupling space is connected via a connecting line of the coupling piece to a second connecting element of the coupling piece, and wherein a base wall of the aforementioned coupling space has at least one opening that is connected or is connectable to the fluid working channel of the handle. This enables the rotational coupling of two different fluids, for example waste air and compressed air, to be transmitted, but at the same time is of compact design and construction.

Preferably, the circumferential wall and the base wall belong to a cup-shaped control part which is arranged via a radial/axial bearing on the coupling pin, and wherein the base wall has spaced-apart control openings that communicate with the connecting line of the coupling pin or with the associated coupling space, and can be connected as desired to control openings of the handle. This enables the throughput of fluids supplied to and/or removed from the handle to be controlled.

Preferably, a light guide runs from the light outlet window to the first connecting element connection-side front face of the light guide. An instrument holder with this feature can be used in conjunction with a supply cable containing a light guide coming from a light source.

Preferably, the light guide extends in a rectilinear inclined bore of the coupling piece from the first connecting element to the central light outlet window. This had the advantage that the light guide contained in the coupling piece has a geometrically simple shape and can easily be inserted into and removed from the coupling piece.

Preferably, electrical leads of electrical first connecting elements of the coupling piece extend to an electrical light source lying substantially on the axis of the coupling bore. Such an instrument holder is suitable for use with supply cables containing electrical supply leads intended for supplying a light source.

Preferably, the electrical leads are arranged on a rod-shaped bulb holder which is inserted in a bulb holder bore that runs along a rectilinear inclined path from the electrical connecting elements to the rotational coupling axis. In this construction, the electrical leads are positioned in a simple manner on a bulb holder carrying the light-generating bulb and that on account of its geometry can very easily be inserted into the coupling piece and removed from the latter to change the bulb.

Preferably, the electrical leads are arranged on a bulb holder that can be inserted in a radial direction in a bulb holder chamber that is formed in the connection-side section of the coupling part, and with its radially inwardly lying section carries the light source, sections of the electrical leads cooperating with contacts that are arranged in one of the boundary surfaces of the bulb holder chamber and that are in turn connected to the electrical connecting elements. This construction facilitates simple installation and dismantling of the bulb holder.

Preferably, the counter-contacts are in each case pretensioned by a spring in the direction of the bulb holder. In this way, a reliable contact with the supply lead is ensured in a simple manner for such a radially movable bulb holder.

Preferably, the bulb holder has holding means in its radially outermost section. This construction facilitates the removal of the bulb holder from the coupling piece when the external surface of the bulb holder rests substantially flush in the external surface of the coupling piece.

Preferably, the electrical connecting elements are carried by a contact plate that is detachably mounted on the front face of the coupling piece. This construction enables a different material to be chosen for a contact plate carrying the electrical connection contacts, than for the securement surface of the fluid connecting element.

Preferably, an optical element, in particular a lens, is inserted, preferably tightly inserted, in the outlet element. This construction has the advantage that light provided by the light source is focused onto the light guide channel arranged centrally in the handle.

Preferably, the instrument holder includes an optical fibre bundle in the light guide channel, the inlet-side front face of the said bundle being located opposite and preferably at a small distance from the light outlet window, and its outlet-side front face being adjacent to the light outlet. In this construction, the channel can accommodate an optical fibre bundle that can easily be bent behind the rotational coupling in order to follow the generally curved shape of the handle, so as to become aligned in the desired manner onto the light outlet point and to be guided past on the inside of the handle, for example on drive shafts or drive motors in the case of a drill holder.

INTRODUCTION TO THE DRAWINGS

DESCRIPTION OF PREFERRED EMBODIMENTS

Figure 1:
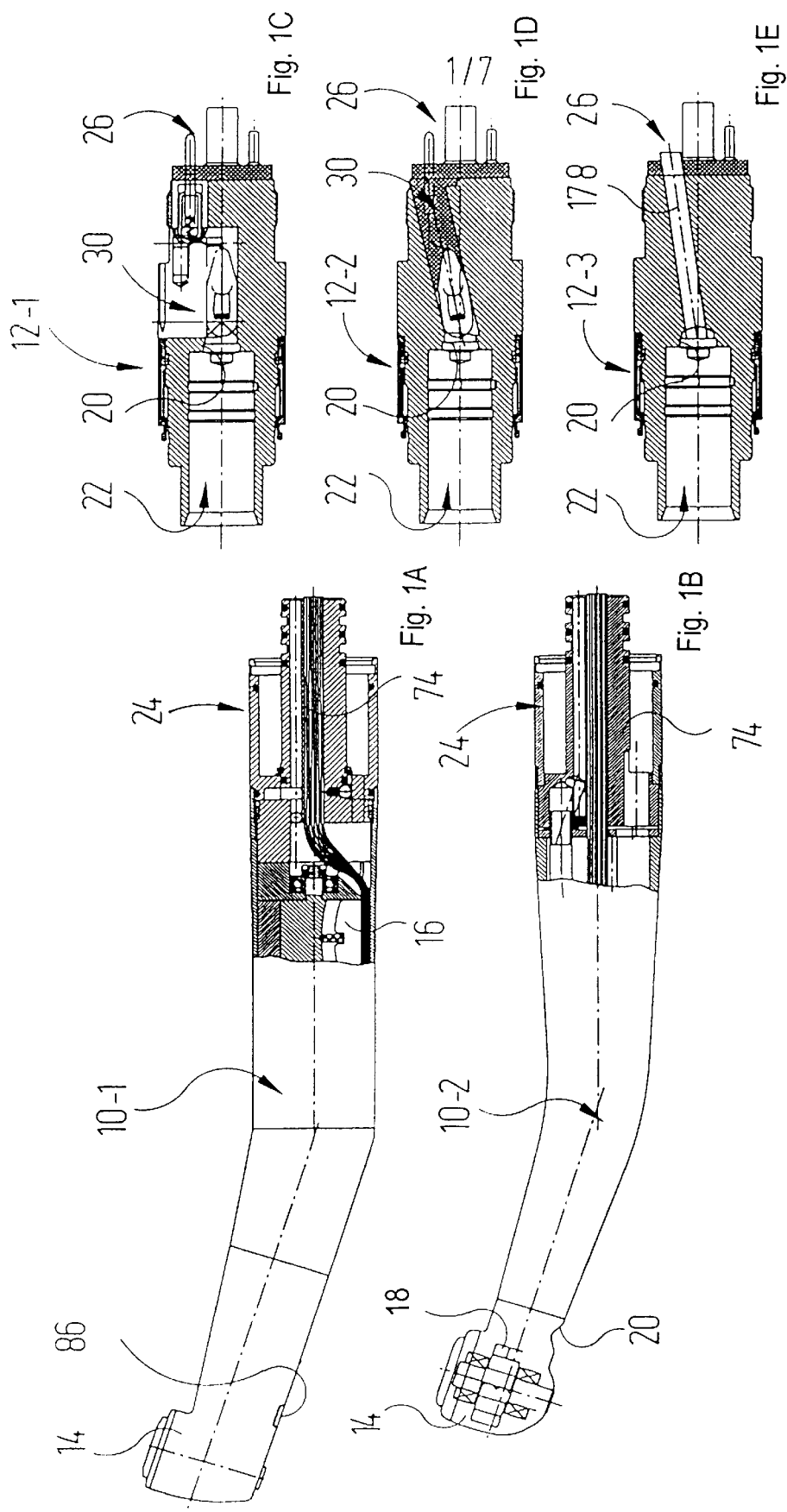
FIGS. 1A–1E show side, partially axially sectioned views of handles and coupling pieces that can be assembled in various combinations to form a dental instrument holder.

FIGS. 1A–1E show handles 10-1 and 10-2 of dental instrument holders that can be connected as desired to different coupling pieces 12-1, 12-2 and 12-3.

The handle 10-1 is a drill handle with a rotating piston air motor 16 distanced from the drill head 14, the said motor driving a drill clamping sleeve arranged in the drill head 14, via shafts and toothed gears (not shown).

The handle 10-2 is likewise a drill handle, in which however the drill clamping sleeve arranged in the drill head 14 is driven by a turbine 18.

The two handles 10-1 and 10-2 otherwise have basically the same geometry, and where hereinafter it is not necessary to make a distinction between the two handles, reference will simply be made to the handle 10.

The coupling pieces 12-1, 12-2 and 12-3 are likewise very similar as regards their mechanical parts, though they differ in the way light is incident on a light outlet window 20, as is described in more detail hereinafter. Here too, in the following description reference will simply be made to a coupling piece 12 where the differences between the various embodiments are not important.

The coupling pieces 12 have in each case a rotational coupling part 22 on the left shown in FIGS. 1C–1E, which cooperates with a substantially complementary rotational coupling part 24 belonging to the handle 10. In its section shown on the right in FIGS. 1C–1E the coupling piece 12 is formed as a plug-in coupling part 26 which cooperates with a complementary plug-in coupling part (not shown in the drawing), which latter is provided at the end of a multi-channel supply cable through which a handle 10 can be supplied with compressed air and light and waste air can be removed.

Details of the rotational coupling parts 22, 24, which together form a rotational coupling 28, as well as details of a light source unit 30 integrated into the coupling piece 12-1, will now be described in more detail with reference to FIG. 2.

The rotational coupling part 22 has a cylindrical outer surface 32 that transforms in the right-hand section into a recessed or set-back outer surface 34 having a threaded portion 36. A circular contact plate 36 is mounted on the right-hand side of the coupling piece 12 shown in FIG. 2, the said contact plate carrying a waste air connecting pipe 38, a water connecting pipe 39, a compressed air connecting pipe 40, a spray air connecting pipe 41, as well as connecting pins 42, 44 which cooperate with corresponding counter plug-in connector parts of the multiple plug-in coupling part (not shown) at the end of the supply cable. A threaded ring (not shown) mounted on the end of the supply cable can be screwed onto the threaded section 36 in order to connect the two plug-in coupling parts of the instrument holder and supply cable firmly to one another. When screwed on, this ring covers a recess 31 in the upper side of the illumination unit 30.

Figure 2:
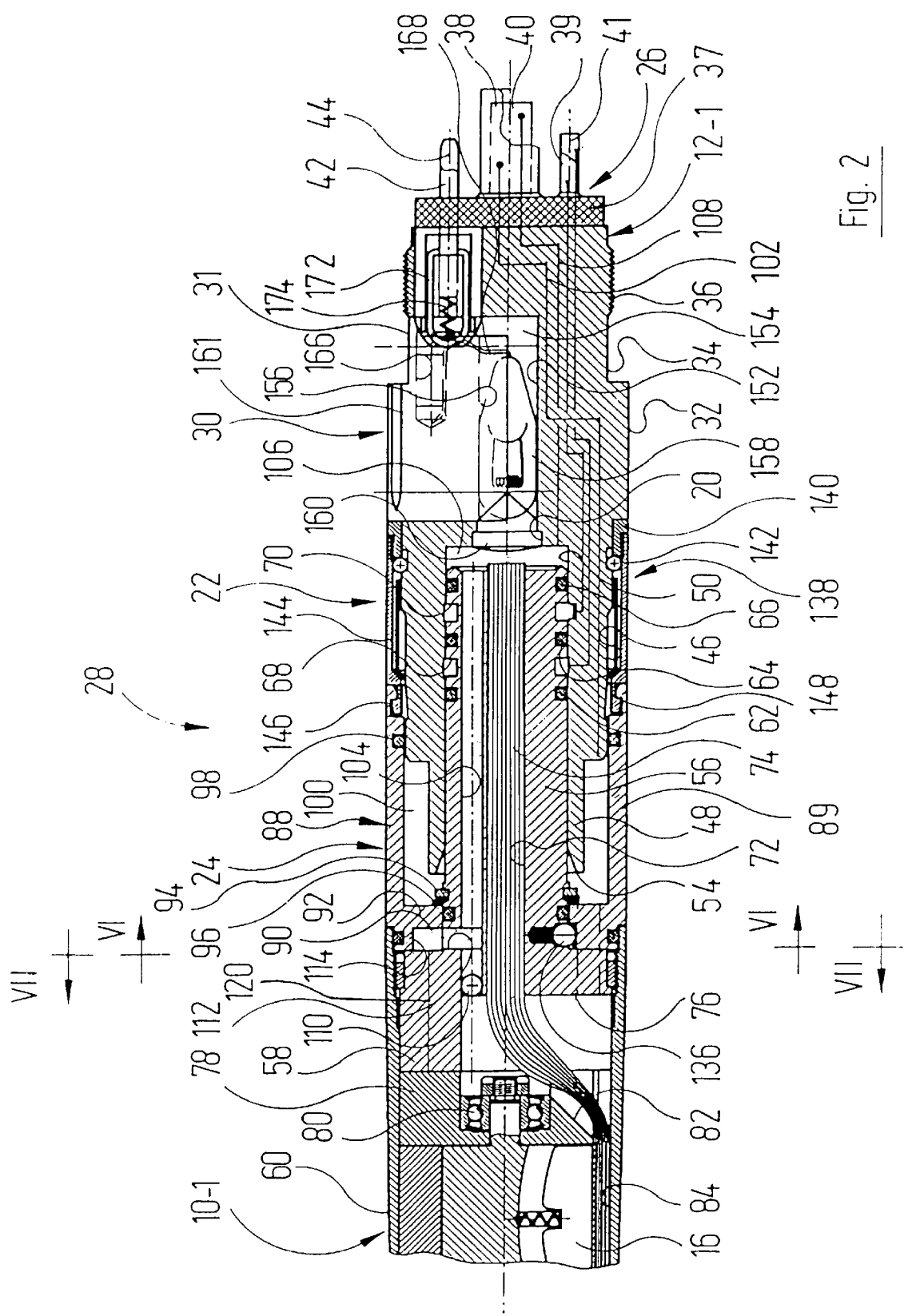
FIG. 2 is an enlarged axial section through the connecting-side end of an assembled instrument holder comprising one of the handles and one of the coupling pieces according to FIG. 1.
Figure 3:
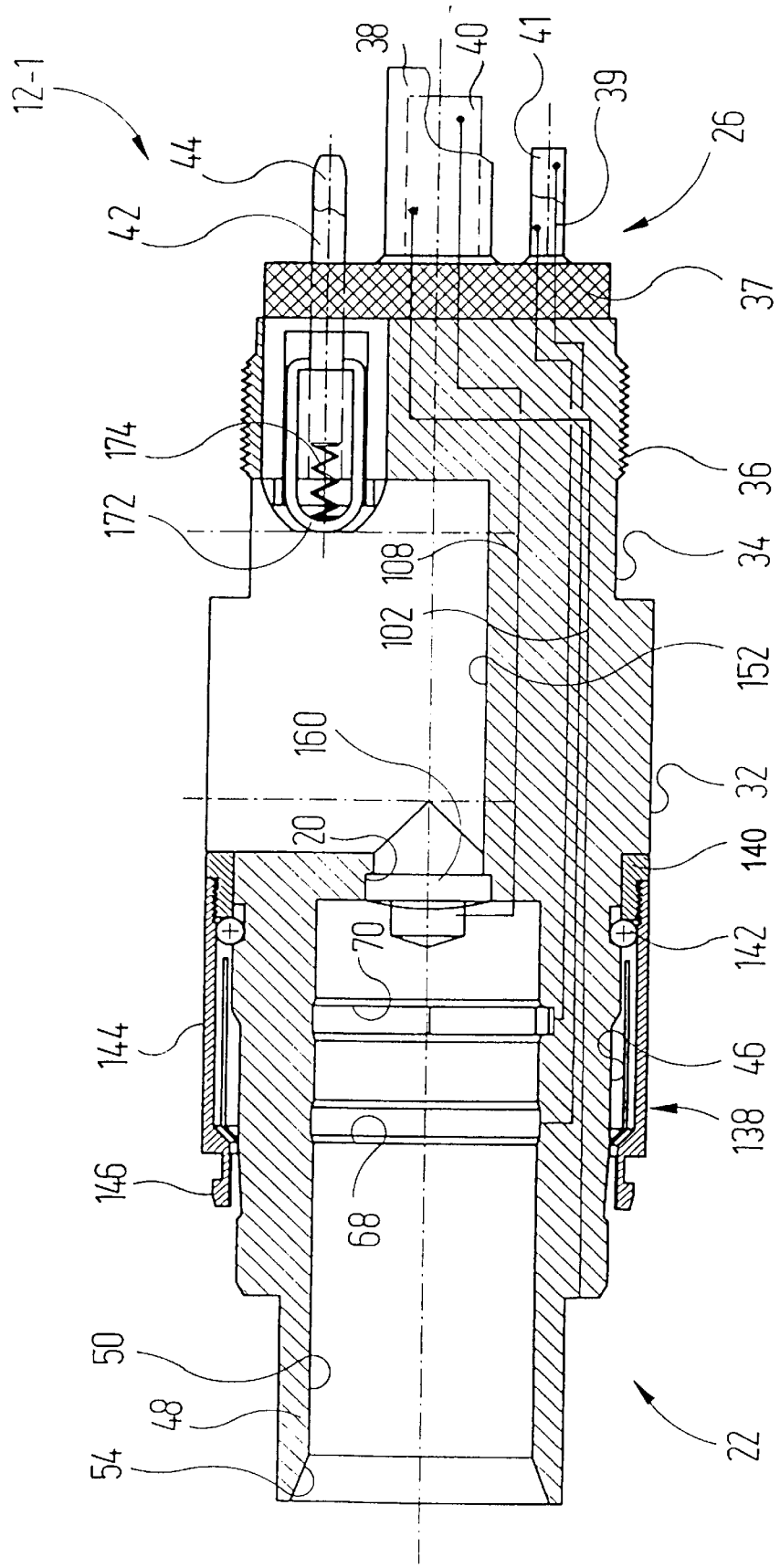
FIG. 3 is an enlarged axial section on a larger scale through one of the coupling pieces shown in FIGS. 1C–1E, without a bulb holder.
Figure 4:
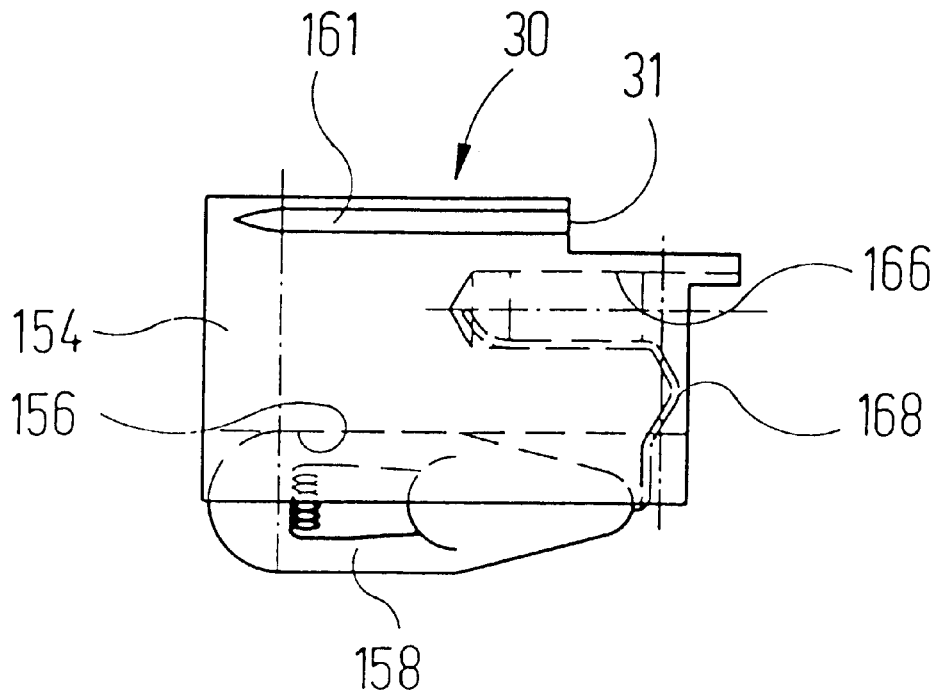
FIG. 4 is a side view of a bulb holder of the coupling piece according to FIG. 3.

In the left-hand section shown in FIG. 2 the coupling piece 12 has a slightly radially inwardly displaced surface section 46, followed by a significantly radially inwardly displaced end section 48.

The region of the coupling piece 12 axially corresponding to the sections 46 and 48 has a centric coupling bore 50 that is designed as a blind bore and has a window 20 in its base or floor or bottom wall. The left-hand end of the coupling bore 50 shown in FIG. 2 is in the form of a cup, as illustrated at 54, in order to facilitate the introduction and engagement of a coupling pin 56. The latter is formed on a front piece 58 that is immovably connected to the end of a housing 60 of the handle 10.

The coupling pin 56 carries in its right-hand end section shown in FIG. 2 three axially spaced apart O-rings 62, 64, 66, which cooperate with the inside wall of the coupling bore. Circumferential grooves 68, 70 are provided between these O-rings, and communicate with the spray air connecting pipe 41 or with the water connecting pipe 39 via lines formed in the coupling piece 12. The grooves 68 and 70 communicate with associated channels in the coupling pin (not shown), which channels feed spray air and water to corresponding discharge points on the working head, which are likewise not shown in the drawing.

The coupling pin 56 has a centric bore 72 in which is arranged an optical fibre bundle 74. This bundle has a flat front face situated opposite the window 20. A chamber 76 is provided in the left-hand end section of the front piece 58 shown in FIG. 2, which chamber runs in the radial direction from the bore 72 to the wall of the housing 60. In like manner a bearing plate 78, which carries one of the bearings 80 of the rotating piston air motor 16, has a recess 82 which together with the chamber 76 forms a deflecting space for the optical fibre bundle 74, by means of which the said optical fibre bundle 74 is bent into a light guide channel 84, in which it extends up to a light outlet point 86 in the vicinity of the drill head 14 (see FIG. 1).

A cup-shaped control element 88 with a circumferential wall 89 is rotatably mounted on the coupling pin 56, which with its centric opening 90 is rotatably mounted on the coupling pin 56, slides with its left-hand front face shown in the drawing on the front face of the front piece 58, and is mounted with the right-hand periphery of its base wall, identified by 92, by means of a retaining ring 94 that engages in the coupling pin 56. A sliding ring 96 is arranged between the right-hand periphery of the base wall 92 and the retaining ring 94.

The right-hand end of the control element 88 in FIG. 2 carries a O-ring 98 that cooperates with the left-hand end of the surface section 46 of the coupling piece 12. In this way the end section 48 of the coupling piece 12 and the cup-shaped control element 88 together define a rotationally symmetrical coupling space 100 that communicates via a connecting channel 102 formed in the coupling piece with the waste air connecting pipe 38.

In the coupling pin 56 a connecting channel 104 is furthermore provided parallel to the bore 72, which channel terminates in the front face of the coupling pin 56 and thereby communicates with a further coupling space 106 defined by the coupling pin 56 and the coupling bore 50. The coupling space 106 communicates via a connecting channel 108 formed in the coupling piece 12 with the compressed air connecting pipe 38.

Figure 6:
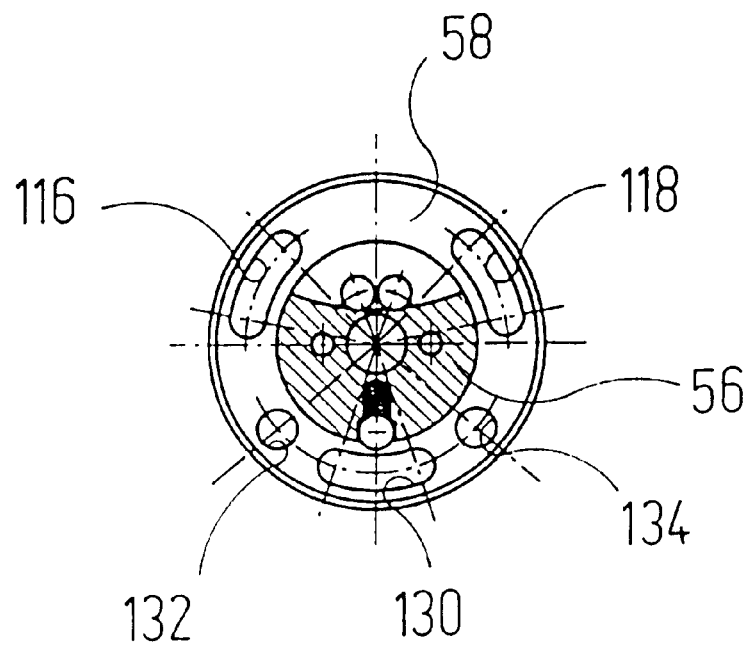
FIG. 6 is a transverse section through a rotational coupling of the instrument holder shown in FIG. 2, along the section line VI—VI.

On the left-hand end in FIG. 1 the connecting channel 104 is closed by a spherical seal 110, communicates just in front of the said spherical seal 110 with a radial channel 112, which in turn communicates at a predetermined setting of the rotatable control element 88 with an opening 114 that terminates in the left-hand front face of the control element 88 in FIG. 2. At a specified angular setting of the control element 88 the opening 114 overlaps one of two openings 116, 118 provided in the free front face of the front piece 58, as can clearly be seen from FIGS. 6 and 7. The control opening 116 communicates via a working channel identified by 120 with a right-hand rotating pressure opening of the rotating piston air motor 16, while the control opening 118 communicates with a left-hand rotating pressure opening of this motor. The compressed air throttling can be predetermined by the extent of this overlap.

In a similar manner the coupling space 100 can be brought into communication as desired with the chamber 76 that communicates with the waste air opening of the rotating piston air motor 16. For this purpose two lateral control slits 126, 128 are provided in the base wall 92 of the control element 88, which slits are curved in the circumferential direction and cooperate with a control slit 130 as well as with control openings 132, 134 arranged laterally with respect to the latter and provided in the front piece 58. The compressed air supplied to the rotating piston air motor 16 as well the waste air flow can both be controlled in this way.

Figure 7:
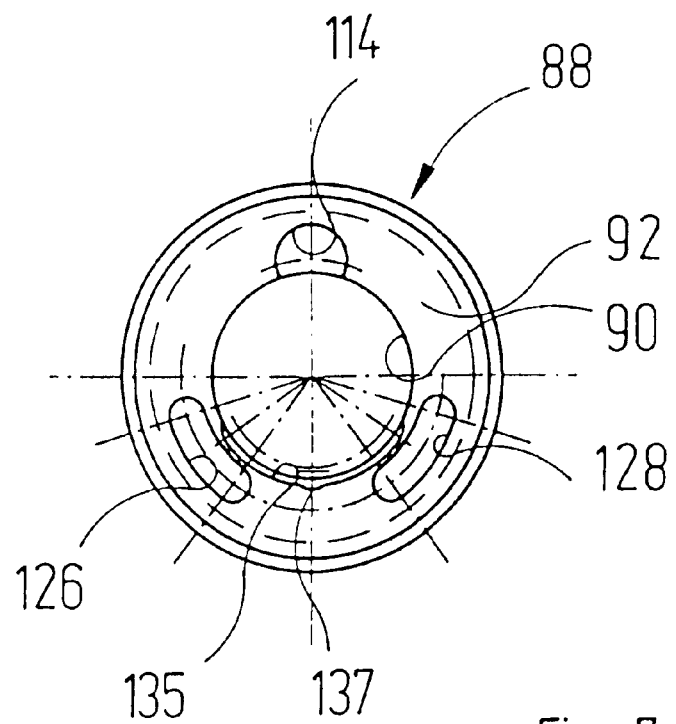
FIG. 7 is a transverse section through the instrument holder illustrated in FIG. 2, along the section line VII—VII.

A spring-loaded, pretensioned retaining sphere 136 that cooperates with a retaining notch 137 shown in FIG. 7 serves to provide tactile detection of the neutral mid-position of the motor control valve formed by the control element 88 and the front piece 58. A stop groove 135 cooperating with the retaining sphere over a limited angular range extends on both sides of the retaining notch.

A locking sleeve 138 is arranged over the surface section 46 of the coupling piece in order to effect axial locking of the handle 10 and coupling piece 12.

This sleeve is screwed onto a threaded ring 140 rotatably connected to the coupling piece 12, a drive ring 142 being arranged between the front face of the threaded ring 140 and an adjacent shoulder of the coupling piece 12, thereby coupling the locking sleeve 138 axially to the coupling piece 12.

Two oppositely located locking arms 144 are sectioned out of the locking sleeve 138, which arms carry at their free end a radially outwardly projecting locking lug 146. The locking lugs cooperate with a complementary locking groove 148 provided on the inside of the circumferential wall of the control element 88. By pressing inwardly simultaneously on the two locking arms 144 the locking lugs 146 are released from the locking groove 148 and the handle 10 and the coupling piece 12 can then be detached from one another in order to attach another handle to the coupling piece 12.

In the right-hand section shown in FIG. 2 a bulb holder chamber 152 is provided in the coupling piece 12, which chamber is substantially cuboid in shape and communicates with the window 20. A bulb holder 154 of complementary cuboid shape is mounted in the bulb holder chamber 152. A groove 156 of semicircular cross-section is formed in the lower side of the bulb holder 154, in which groove one half of a cold-light incandescent bulb 158 is arranged so that its coil lies on the axis of the window 20, and thus also on the axis of the optical fibre bundle 74, when the bulb holder 154 is in place. In order to seal the bulb holder chamber 152 with respect to the connecting space 106 and to focus the coil of the incandescent lamp 158 onto the front face of the optical fibre bundle 74, a lens 160 is mounted in the window 20.

Figure 5:
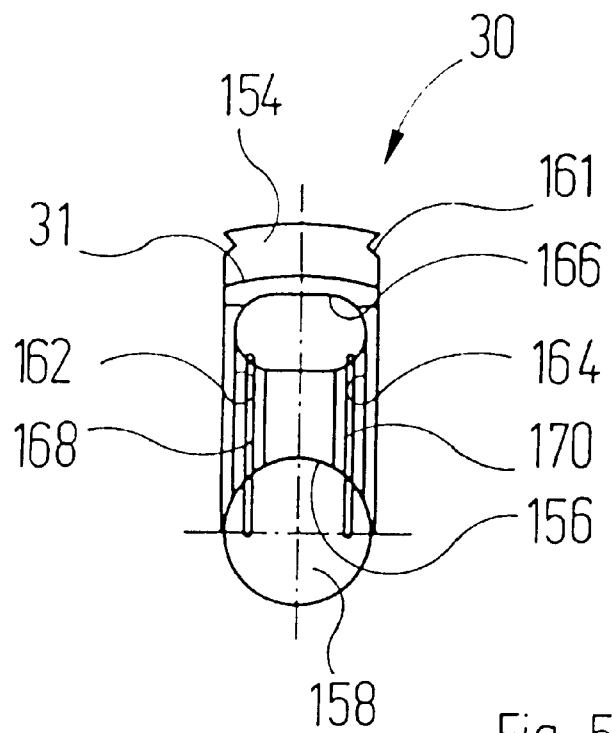
FIG. 5 is a view of the connecting-side front face of the bulb holder according to FIG. 4.

The side surfaces of the bulb holder 154 have longitudinally extending holding grooves 161 that are accessible by flattening the adjacent circumferential section of the outside of the coupling piece 12. Two narrow grooves 162, 164 are provided in the right-hand front face, shown in the drawing, of the bulb holder 154, which grooves terminate in an upper front face recess 166. The connecting lugs 168, 170 of the incandescent bulb 158 lie in the grooves 162 and 164, as can be seen in particular in FIG. 5. The ends of the connecting lugs 168, 170 lie in the front face recess 166.

Two contact bridges 172 rest against the connecting lugs 168, 170 when the bulb holder 154 is mounted in the bulb holder chamber 152, each of the contact bridges being pretensioned by a spring 174 in the retracted position and running in a displaceable manner on extensions of the connecting pins 42, 44. In this way the connecting lugs 168, 170 can be detachably connected to the corresponding supply leads of the supply cable.

It can be seen that the light transmission between the incandescent bulb 58 and the light outlet point 86 of the handle 10 occurs independently of the angular position of the handle 10 relative to the coupling piece 12, and that the incandescent bulb 158 can easily be replaced if necessary.

In operation the rotating piston air motor 16 can be controlled by adjusting the control element 88, the relative position between the control element 88 and the housing 60 of the handle 10 being important as regards this control. This relative position is independent of the angular setting in each case of the handle 10 on the coupling piece 12, which simplifies the visual monitoring and control of the rotational speed setting.

Figure 8:
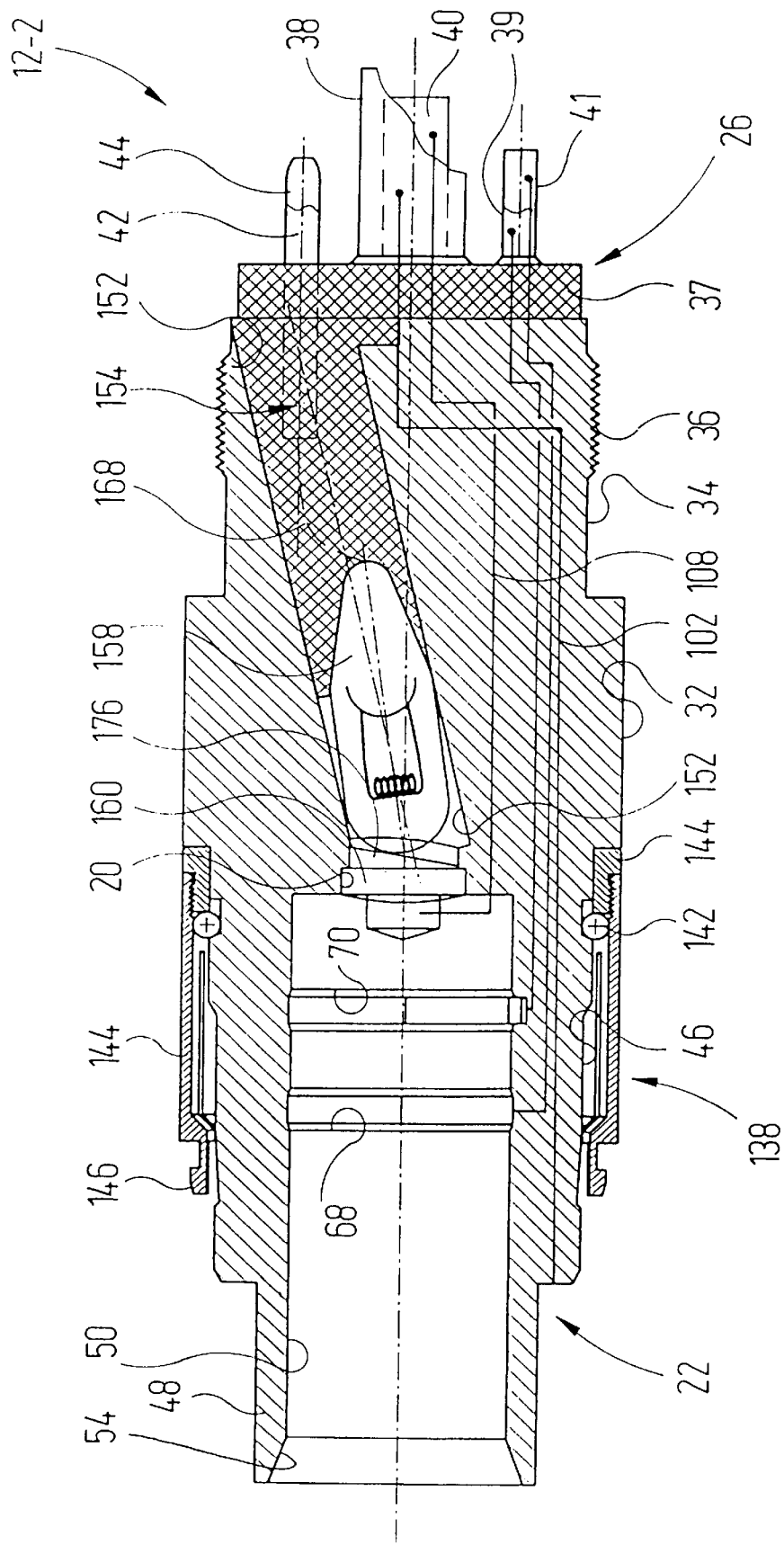
FIGS. 8 and 9 are similar views to those of FIG. 6, in which however modified coupling pieces are reproduced that are already shown on a smaller scale in FIGS. 1C–1E.
Figure 9:
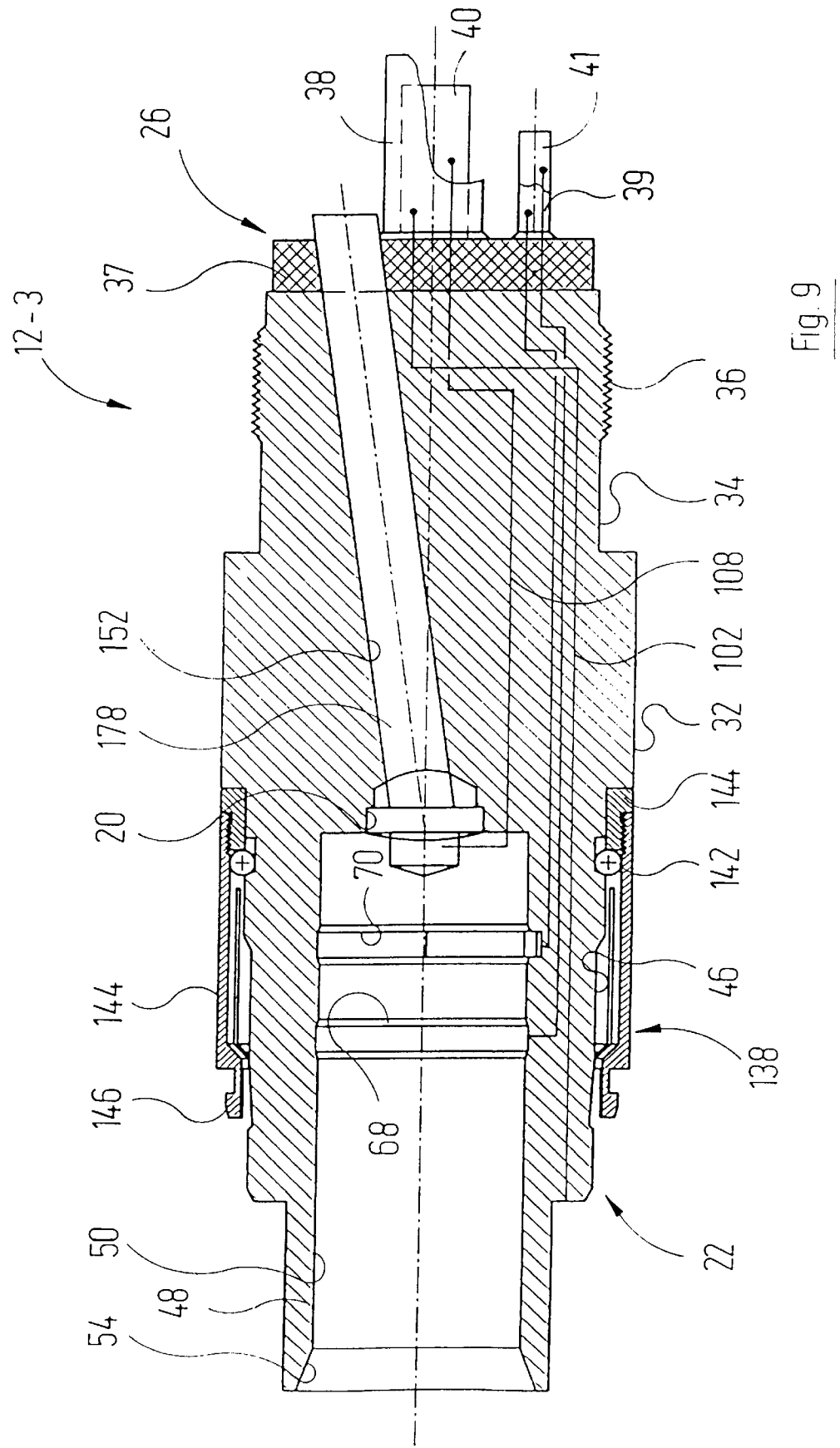

In the embodiments according to FIGS. 8 and 9 those parts of the coupling piece 12-2 and 12-3 that correspond functionally to the aforedescribed parts of the coupling piece 12-1 are again provided with the same reference numerals, even if they differ in geometrical detail from the previously described parts.

With the embodiment illustrated in FIG. 8 the bulb holder 154 is rod-shaped and the bulb holder chamber 152 is correspondingly formed as a bore that runs in a rectilinear and inwardly radially inclined manner from the connecting pins 42, 44 to the axis of the coupling bore 50. The incandescent bulb 158 and its connecting lugs 168, 170 are firmly embedded in the material of the bulb holder 154, which together with the contact plate 36 and the connecting pins 42, 44 forms a disposable part. This feature too ensures a simple and easy replacement of the incandescent bulb.

As regards the light emission, there are only a few slight changes in the arrangement compared to the embodiment according to FIGS. 2 to 7. The tilting of the axis of the incandescent bulb 158 relative to the axis of the coupling bore 50 can—if desired—be compensated by a prism 176, which is preferably secured to the flat side of the lens 160.

In the embodiment according to FIG. 9 a light guide 178 is inserted into a light guide bore 152 inclined outwardly from the axis of the coupling bore 50, the front faces of the light guide lying in a plane transverse to the axis of the coupling bore 50. After the connection of a supply cable to the coupling piece 12 the right-hand front face 178 lies opposite the emission end of an optical fibre bundle (not shown in the drawing) contained in the supply cable, which bundle leads to a cold light bulb in a spatially separately installed supply unit.

It can be seen that the aforedescribed embodiments likewise satisfy three functions:

ability of the handle 10 to be plugged into the coupling piece 12 and thus to connect the handle 10 to the supply cable at any other arbitrary angular position;

supply of compressed air to the handle independently of the angular position of the handle relative to the coupling piece;

removal of waste air from the handle through the coupling piece independently of the angular position of the handle relative to the coupling piece;

delivery of light to the handle independently of the angular position of the handle relative to the coupling piece.

What is claimed is:

1. An instrument holder, comprising:

a handle (10) having a working head (14) mounted on said handle, a light outlet (86), and at least one additional energy consumer (18), a coupling piece (12) connectable to a counter-coupling piece through which an energy supply cable is arranged to be connected to the instrument holder, said coupling piece (12) comprising a first connection (42, 44) serving to supply electrical energy for emitting light from said light outlet (86), and at least one second connection (38,40) radially spaced from said first connection (42, 44) and serving to supply air to or remove waste medium from said additional energy consumer (18), a rotational coupling (28) through which said coupling piece (12) is detachably connected to said handle (10), said rotational coupling (28) comprising a first coupling portion (24) on said handle and a second coupling portion (22) on said coupling piece (12), one of said coupling portions having a coupling pin (56) and the other of said coupling portions having a coupling bore (50) complementary to said coupling pin (56) so that said coupling pin (56) and said coupling bore (50) are displaceable relative to each other in an axial direction and rotatable relative to each other in a circumferential direction, a light outlet window (20) in a bottom wall of said coupling bore (50), said coupling pin (56) having a central light guide channel (72) axially aligned with said light outlet window (20), an eccentric connecting line (104) in said coupling pin (56) or in a wall surrounding said coupling bore (50), said eccentric connecting line (104) having one end adjacent to said other coupling portion (22) that is connected, via a first coupling space (106) that is rotationally symmetrical relative to a rotational coupling axis of said instrument holder, into a working channel of said handle leading from said first coupling space (106) to said additional energy consumer (18), an electrical light source lying substantially on an axis of said coupling bore (50), and electric leads extending from said first connection (42, 44) to said electrical light source.

2. The instrument holder according to claim 1, in which said first coupling space (106) is connected via a connecting line (102) to said second connection (38, 40).

3. The instrument holder according to claim 1, further comprising a locking device (138) that axially locks said coupling piece (12) and said handle (10) when said first and second coupling portions (22, 24) are fully engaged.

4. The instrument holder according to claim 3, in which said locking device (138) comprises at least one radially movable locking lug (146) carried on one of said coupling portions and a locking groove (148) on the other of said coupling portions that fully encircles and cooperates with said locking lugs.

5. The instrument holder according to claim 4, in which said locking device includes two diametrically opposite locking lugs (146) that cooperate in a similar manner to each other with said locking groove.

6. The instrument holder according to claim 4, wherein said locking device (138) includes actuating arms (144) lying flush on an outside of one of said coupling portions (22, 24) and carrying said locking lugs.

7. The instrument holder according to claim 4, further comprising a locking sleeve that carries said locking lugs (146) and at least partially overlaps a radially set-back surface portion of one of said coupling portions that carries said locking lugs (146) and is coupled with said one coupling portion that carries said locking lugs (146) to move jointly in an axial direction.

8. The instrument holder according to claim 1, in which said additional energy consumer (18) comprises a fluid driven energy consumer, and said coupling pin (56) and said coupling bore (50) are sealed with respect to one another and define said first coupling space (106) between them, in which said connecting line (104) in said coupling pin and said connecting line (108) leading to said second connecting element terminate.

9. The instrument holder according to claim 1, in which said second coupling portion (22) contains said coupling bore (50), has a circumferential surface (46) setback relative to an outer surface (32) of said coupling piece and cooperates tightly with and at least partially overlaps a circumferential wall (88) of said first coupling portion (24) that carries said coupling pin (56).

10. The instrument holder according to claim 9, in which said second coupling portion (22) containing said coupling bore (50) has an end-section (48) of reduced diameter compared to said circumferential set-back surface (46) to define a second coupling space (100) between said circumferential wall (88) and said end section (48) of reduced diameter, a connecting line (102) connects said second coupling space (100) to said second connecting element (38, 40) and a base wall (92) for said second coupling space (100) has at least one opening connectable into a fluid working channel of said handle (10).

11. The instrument holder according to claim 10, in which said circumferential wall (88) and said base wall (92) comprise a cup-shaped control (88) that is arranged on said coupling pin (56) via a radial/axial bearing (94) on said coupling pin (56), and said base wall (92) has spaced-apart control openings (126, 128) that communicate with said connecting line (104) of said coupling pin (56) or with said second coupling space (100) and can be connected as desired to control openings (116, 118) of said handle (10).

12. The instrument holder according to claim 1, in which said electrical leads are arranged on a rod-shaped holder that is inserted in a bulb holder (154) that runs from said first connection (42, 44) along a rectangular path (152) inclined to said rotational coupling axis.

13. An instrument holder as claimed in claim 1, further comprising a bulb holder (30) on which said electrical leads are arranged, said bulb holder (30) being insertable in a radial direction in a bulb holder chamber (152) that is formed in a connection-side section of said coupling piece (12) and having a radially inwardly lying section that carries a light source, sections of said electrical leads cooperating with contacts (168) arranged in a boundary surface of said bulb holder chamber (152) and being connected to said connection (42, 44).

14. An instrument holder as claimed in claim 13, further comprising counter-contacts (172) pretensioned by a spring (174) in a direction of said bulb holder (30).

15. An instrument holder as claimed in claim 13, in which said bulb holder (30) has holding means (161) in its radially outmost section.

16. An instrument holder as claimed in claim 1, in which said electrical connecting element (42, 44) is carried by a contact plate (37) that is detachably mounted on an end face of said coupling piece (12).

17. An instrument holder as claimed in claim 1, further comprising an optical element inserted in said outlet element (86).

18. An instrument holder as claimed in claim 1, further comprising an optical fiber bundle (74) in said light guide channel (72), having an inlet-side front face located opposite and at a small distance from said outlet window (20) and an outlet-side front face adjacent to said light outlet (86).

19. An instrument holder, comprising:

a handle (10) having a working head (14) mounted on said handle, a light outlet (86), and at least one additional energy consumer (18), a coupling piece (12) connectable to a counter-coupling piece through which an energy supply cable is arranged to be connected to the instrument holder, said coupling piece (12) comprising a first connection (42, 44) serving to supply electrical energy for emitting light from said light outlet (86), and at least one second connection (38,40) radially spaced from said first connection (42, 44) and serving to supply air to or remove waste material from said additional energy consumer (18), a rotational coupling (28) through which said coupling piece (12) is detachably connected to said handle (10), said rotational coupling (28) comprising a first coupling portion (24) on said handle and a second coupling portion (22) on said coupling piece (12), one of said coupling portions having a coupling pin (56) and the other of said coupling portions having a coupling bore (50) complementary to said coupling pin (56) so that said coupling pin (56) and said coupling bore (50) are displaceable relative to each other in an axial direction and rotatable relative to each other in a circumferential direction, a light outlet window (20) in a bottom wall of said coupling bore (50), said coupling pin (56) having a central light guide channel (72) axially aligned with said light outlet window (20), an eccentric connecting line (104) in said coupling pin (56) or in a wall surrounding said coupling bore (50), said eccentric connecting line (104) having one end adjacent to said other coupling portion (22) that is connected, via a first coupling space (106) that is rotationally symmetrical relative to a rotational coupling axis of said instrument holder, into a working channel of said handle leading from said first coupling space (106) to said additional energy consumer (18), and a light guide (178) running from said light outlet window (20) to a front face of said light guide (178) facing towards said first connection (42, 44).

* * * * *